United States Patent
Toyohara et al.

(10) Patent No.: US 9,974,935 B2
(45) Date of Patent: May 22, 2018

(54) MICRONEEDLE AND MICRONEEDLE ARRAY

(71) Applicants: TEIJIN LIMITED, Osaka (JP); MEDRx Co., Ltd., Kagawa (JP)

(72) Inventors: Kiyotsuna Toyohara, Tokyo (JP); Taishi Tanaka, Tokyo (JP); Kazuteru Kohno, Tokyo (JP); Takashi Oda, Tokyo (JP); Koichi Masaoka, Tokyo (JP); Katsunori Kobayashi, Kagawa (JP); Masaki Ishibashi, Kagawa (JP); Hidetoshi Hamamoto, Kagawa (JP)

(73) Assignee: MEDRX CO., LTD., Kagawa (JP)

( * ) Notice: Subject to any disclaimer, the term of this patent is extended or adjusted under 35 U.S.C. 154(b) by 845 days.

(21) Appl. No.: 14/396,294

(22) PCT Filed: Apr. 24, 2013

(86) PCT No.: PCT/JP2013/062735
§ 371 (c)(1),
(2) Date: Oct. 22, 2014

(87) PCT Pub. No.: WO2013/162053
PCT Pub. Date: Oct. 31, 2013

(65) Prior Publication Data
US 2015/0094648 A1  Apr. 2, 2015

(30) Foreign Application Priority Data
Apr. 25, 2012  (JP) ................. 2012-099489

(51) Int. Cl.
*A61M 37/00* (2006.01)
*A61K 9/00* (2006.01)

(52) U.S. Cl.
CPC ....... *A61M 37/0015* (2013.01); *A61K 9/0021* (2013.01); *A61M 2037/0046* (2013.01); *A61M 2037/0053* (2013.01); *A61M 2037/0061* (2013.01)

(58) Field of Classification Search
None
See application file for complete search history.

(56) References Cited

U.S. PATENT DOCUMENTS 8,834,423 B2 *  9/2014  Falo, Jr. ............ A61M 37/0015
                                                        604/173
2008/0221532 A1  11/2008  Ogawa
2012/0265145 A1  10/2012  Mefti et al.

FOREIGN PATENT DOCUMENTS

| JP | 2007-130030 | 5/2007 |
| JP | 2007-190112 | 8/2007 |
| JP | 2007-260351 | 10/2007 |
| JP | 2008-49646 | 3/2008 |
| JP | 2008-142183 | 6/2008 |
| JP | 2010-29634 | 2/2010 |
| JP | 2010-69270 | 4/2010 |
| WO | 2006/055799 | 5/2006 |
| WO | 2006/138719 | 12/2006 |
| WO | 2007/012114 | 2/2007 |
| WO | 2011/076537 | 6/2011 |
| WO | 2011/150144 | 12/2011 |

OTHER PUBLICATIONS

Donnelly, R., et al., Journal of Controlled Release 147: 333-341 (2010). (Year: 2010).*
Davidson, A., et al., Chemical Engineering Research and Design 86: 1196-1206 (2008). (Year: 2008).*
Office Action dated Feb. 1, 2016 in Chinese Application No. 201380021527.6, with English translation.
International Search Report dated Aug. 6, 2013 in corresponding to International application No. PCT/JP2013/062735.
Patent Cooperation Treaty International Preliminary Report on Patentability dated Nov. 6, 2014 in corresponding to International application No. PCT/JP2013/062735.
Extended European Search Report dated Nov. 10, 2015 in European Application No. 13782340.7.

* cited by examiner

*Primary Examiner* — David J Blanchard
*Assistant Examiner* — Daniel F. Coughlin
(74) *Attorney, Agent, or Firm* — Wenderoth, Lind & Ponack, L.L.P.

(57) ABSTRACT

The present invention relates to a microneedle and a microneedle array. More specifically, it relates to a microneedle and a microneedle array capable of injecting a drug into the surface layer or horny layer of the skin easily, safely and efficiently.

12 Claims, 10 Drawing Sheets

MICRONEEDLE AND MICRONEEDLE ARRAY

TECHNICAL FIELD

The present invention relates to a microneedle and a microneedle array. More specifically, it relates to a microneedle and a microneedle array capable of injecting a drug into the surface layer or horny layer of the skin easily, safely and efficiently.

A microneedle and a microneedle array which can support not only a drug but also a stabilizer and a thickener in large quantities and have excellent puncture property.

The microneedle is used to administer a drug transdermally and comprises a top section, a shaft section and a base section, wherein
(i) the tip apex angle ($\alpha$) is 15 to 60°;
(ii) the tip diameter ($D_0$) is 1 to 20 μm;
(iii) the area ($A_3$) of the top surface of the base section is larger than the area ($A_2$) of the bottom surface of the shaft section;
(iv) the following expressions (1) and (2) are satisfied $$H/D_4 \geq 3 \tag{1}$$

(H is the overall height, and $D_4$ is the diameter of the bottom surface of the base section)

$$\beta \geq 90 - 0.5\alpha \tag{2}$$

($\beta$ is the angle formed between the side surface of the shaft section and the top surface of the base section, and $\alpha$ is the tip apex angle.); and
(v) a solid composition containing a drug is fixed to the side surface of the shaft section and the following expression (5) is satisfied.

$$10° \leq \gamma \leq 60° \tag{5}$$

($\gamma$ is the angle formed by tangent lines connecting the apex of the top section and the surface of the solid composition fixed to the side surface of the shaft section.)

BACKGROUND ART

Heretofore, to administer a drug or the like to the biological surface of a patient, that is, the surface of the skin or mucous membrane, a method of applying a liquid substance or a powdery substance has been employed in most cases. However, since the area to which a drug can be applied is limited to the surface of the skin, a patient experiences a daily basis the fall-off of the applied drug by perspiration or contact with foreign matter, thereby making it difficult to administer a suitable amount of a drug effectively.

As an alternative to the application of a drug to the biological surface, there is proposed the administration of a drug into a living body by means of a microneedle. Also, proposals have been made to improve the puncture property of the microneedle.

For instance, in the methods of Patent Document 1 and Patent Document 2, there are proposed a microneedle and a microneedle array both of which are hardly broken and bent. However, the Puncture properties of the microneedle and the microneedle array are not satisfactory.

Patent Document 3 proposes a method of facilitating puncture by curving a conical surface or a pyramid surface toward the inside of a microneedle. However, since the method disclosed by Patent Document 3 makes use of volume shrinkage when a polymer solution is applied to a stamper to be gelled and dried, it is not suitable for a thermoplastic resin.

Patent Document 4 discloses a microneedle which is formed from a water-soluble or water-swellable resin, shaped like a spindle, a truncated pyramid or a conical pyramid and coated with a lubricant component.

Patent Document 5 discloses a method of administering a drug beneath the epidermis by loading a microneedle with a drug efficiently. This is a technology which can be applied to a liquid drug but not satisfactory as a technology which can achieve puncture property, the amount of the loaded drug and medication property for a solid drug.

(Patent Document 1) JP-A 2007-130030
(Patent Document 2) JP-A 2007-190112
(Patent Document 3) JP-A 2008-142183
(Patent Document 4) JP-A 2010-029634
(Patent Document 5) JP-A 2007-260351

DISCLOSURE OF THE INVENTION

It is an object of the present invention to provide a microneedle and a microneedle array which can be thrust into the epidermal layer of a patient smoothly, have safety and simplicity and are able to administer a predetermined drug without pain. It is another object of the present invention to provide a microneedle and a microneedle array which can support not only a drug but also a stabilizer or a thickener in large quantities and have excellent puncture property. It is a further object of the present invention to provide a microneedle device including a microneedle array.

The present invention is a microneedle for administering a drug transdermally, which comprises a top section, a shaft section and a base section, wherein
(i) the tip apex angle ($\alpha$) is 15 to 60°;
(ii) the tip diameter ($D_0$) is 1 to 20 μm;
(iii) the area ($A_3$) of the top surface of the base section is larger than the area ($A_2$) of the bottom surface of the shaft section;
(iv) the following expressions (1) and (2) are satisfied;

$$H/D_4 \geq 3 \tag{1}$$

(H is the overall height, and $D_4$ is the diameter of the bottom surface of the base section.)

$$\beta \geq 90 - 0.5\alpha \tag{2}$$

($\beta$ is the angle between the side surface of the shaft section and the top surface of the base section, and $\alpha$ is the tip apex angle.); and
(v) a solid composition containing the drug is fixed to the side surface of the shaft section and the following expression (5) is satisfied.

$$10° \leq \gamma \leq 60° \tag{5}$$

($\gamma$ is the angle formed by tangent lines connecting the apex of the top section and the surface of the solid composition fixed to the side surface of the shaft section.)

The present invention is also a microneedle array including a plurality of the above microneedles.

EXPLANATION OF SYMBOLS $D_0$: tip diameter
$D_1$: diameter of bottom surface of top section
$D_2$: diameter of bottom surface of shaft section
$D_3$: diameter of top surface of base section
$D_4$: diameter of bottom surface of base section
H: overall height
$H_1$: height of top section
$H_2$: height of shaft section
$H_3$: height of base section
α: tip apex angle
β: angle between side surface of shaft section and top surface of base section
γ: angle formed by apex of top section and topmost layer of solid composition fixed to side surface of shaft section
δ: angle formed by lines connecting apex of top section and the surface of solid composition fixed to top section

BEST MODE FOR CARRYING OUT THE INVENTION

The microneedle of the present invention is a drug supporting microneedle in which a solid composition comprising a drug is fixed to the side surface of the shaft section. The microneedle supporting a drug may be referred to as "supporting microneedle". The microneedle before supporting a drug may be simply referred to as "microneedle". The same can be said of the microneedle array.

<Microneedle>

Figure 1:
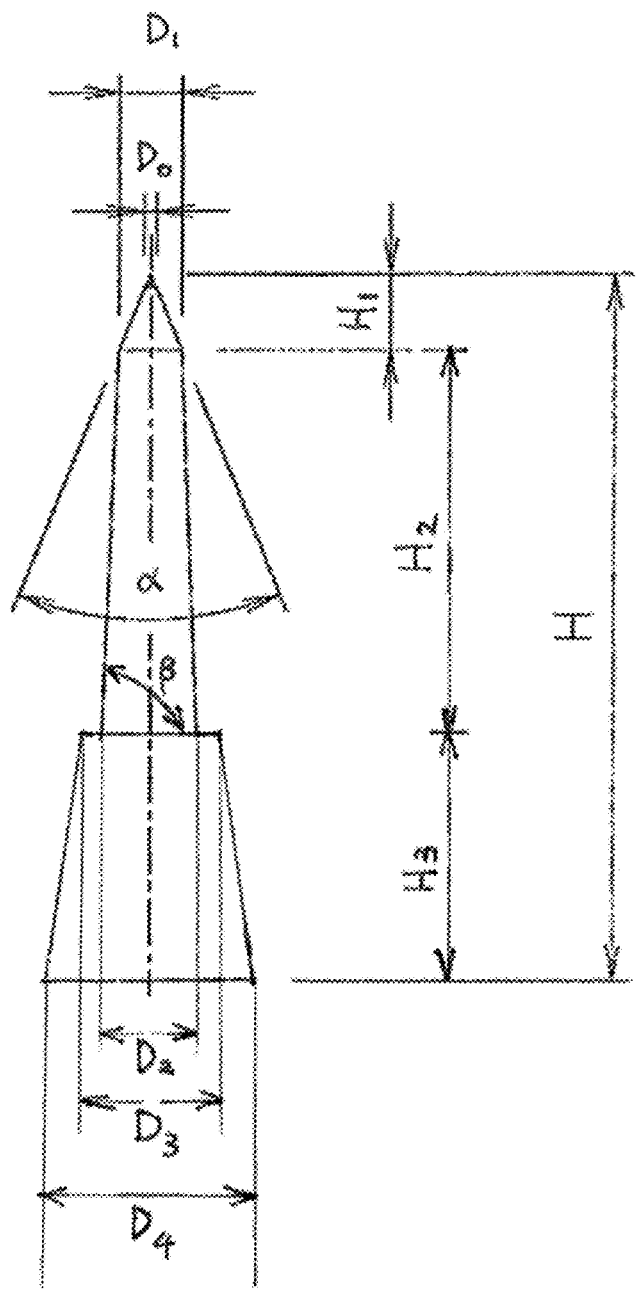
FIG. 1 is a schematic diagram of the microneedle of the present invention.
Figure 2:
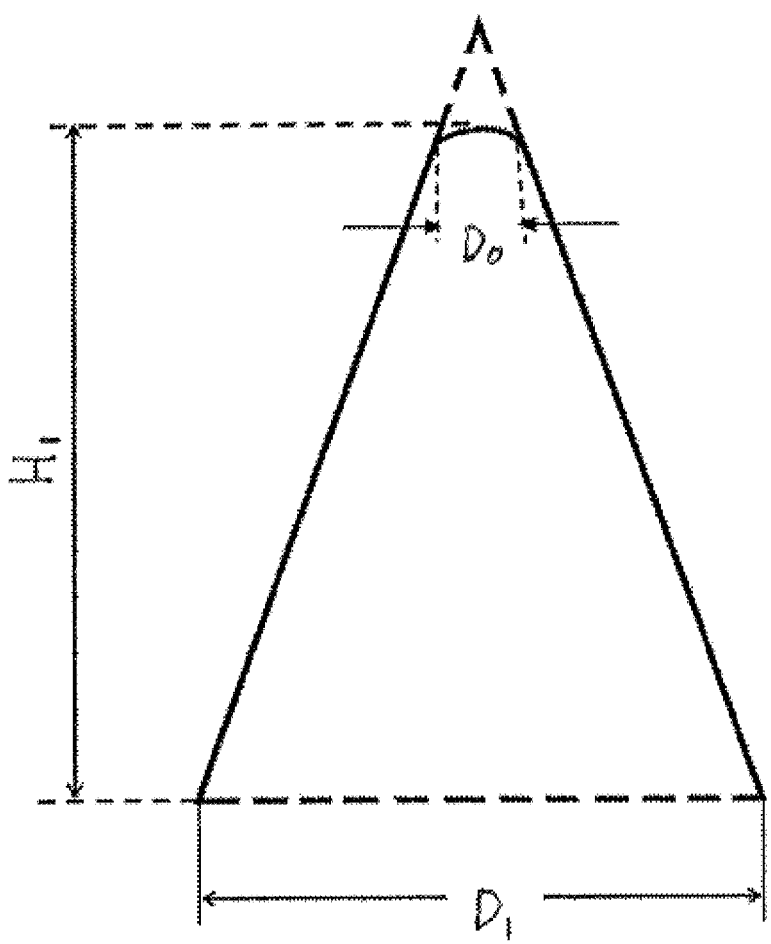
FIG. 2 is a schematic diagram of the top section of the microneedle of the present invention.

The microneedle will be explained with reference to FIG. 1. FIG. 1 is an overall view of the microneedle. The microneedle has a base section, a shaft section for supporting a drug, which is formed on the base section, and a top section for puncturing the skin, which is formed on the shaft section, and all of the three sections are unified.

(Base Section)

The base section may be shaped like a polygonal truncated pyramid such as a triangular, quadrangular or hexagonal truncated pyramid, or conical truncated pyramid. The diameter ($D_4$) of the bottom surface of the base section is preferably 30 to 500 μm, more preferably 100 to 250 μm. The diameter ($D_3$) of the top surface of the base section is preferably 30 to 500 μm, more preferably 90 to 240 μm. The height ($H_3$) of the base section is preferably 35 to 600 μm, more preferably 100 to 500 μm. The diameter ($D_4$) of the bottom surface of the base section is a diameter when the bottom surface of the base section is approximated to a circular surface. The diameter ($D_3$) of the top surface of the base section is a diameter when the top surface of the base section is approximated to a circular surface.

(Shaft Section)

The shaft section may be shaped like a polygonal truncated pyramid such as a triangular, quadrangular or hexagonal truncated pyramid, or conical truncated pyramid. The shaft section has a pedestal shape so that the top section can be mounted on the top part thereof. The diameter ($D_2$) of the bottom surface of the shaft section is preferably 25 to 450 μm, more preferably 25 to 235 μm. The diameter ($D_2$) of the bottom surface of the shaft section is a diameter when the bottom surface of the shaft section is approximated to a circular surface. The diameter ($D_1$) of the top surface of the shaft section is the same as the diameter ($D_1$) of the bottom surface of the top section. The height ($H_2$) of the shaft section is preferably 50 to 600 μm, more preferably 50 to 500 μm, much more preferably 50 to 240 μm. The shaft section has the function of fixing a drug to the wall thereof and carrying the drug to a predetermined administration position.

(Top Section)

The top section may be shaped like a polygonal truncated pyramid such as a triangular, quadrangular or hexagonal truncated pyramid, or conical truncated pyramid. The diameter ($D_1$) of the bottom surface of the top section is preferably 1 to 170 μm, more preferably 10 to 80 μm. The diameter ($D_1$) of the bottom surface of the top section is a diameter when the bottom surface of the top section is approximated to a circular surface. The height ($H_1$) of the top section is preferably 1 to 640 μm, more preferably 10 to 150 μm.

The tip diameter ($D_0$) is 1 to 20 μm. From the viewpoint of enhancing the effect of puncturing the epidermal layer of a patient smoothly, the tip diameter ($D_0$) is preferably 1 to 10 μm. When the tip diameter ($D_0$) is larger than 20 μm, resistance at the time of puncturing the skin becomes large, whereby it is difficult to puncture the skin and the tip tends to deform disadvantageously.

The tip apex angle (α) is 15 to 60°, preferably 30 to 60°. When the tip apex angle (α) falls within the range of 30 to 45°, a more excellent effect is obtained. When the tip apex angle (α) is outside the range of 15 to 60°, resistance at the time of puncturing the skin becomes large, whereby it is difficult to puncture the skin and the tip tends to deform disadvantageously.

(Overall Height)

The overall height (H) is the sum of the thickness (X) of the skin when the effect of a drug is developed efficiently and the length (Y) of room in consideration of sagging skin when the microneedle is slowly inserted into the skin without pain. X is preferably 15 to 800 μm, more preferably 100 to 500 μm. Y is preferably 30 to 500 μm, more preferably 50 to 300 μm. The overall height (H) is preferably 120 to 800 μm, more preferably 150 to 500 μm.

(Expressions (1) and (2))

The microneedle satisfies the following expression (1).

(1) $H/D_4 \geq 3$ (H: overall height, $D_4$: diameter of bottom surface of base section)

The upper limit of $H/D_4$ is preferably not more than 20 from the viewpoints of the object of the present invention and moldability. When $H/D_4$ is less than 3, resistance at the time of puncturing the skin becomes large, whereby it is difficult to puncture the skin and the tip of the microneedle tends to deform, which is inconvenient in terms of object and effect. $H/D_4$ is preferably 3 to 10, more preferably 3 to 6.

The microneedle satisfies the following expression (2)

$$\beta \geq 90 - 0.5\alpha \tag{2}$$

In the expression (2), β is the angle between the side surface of the shaft section and the top surface of the base section as shown in FIG. 1. α is the tip apex angle. In the microneedle, the area ($A_3$) of the top surface of the base section is larger than the area ($A_2$) of the bottom surface of the shaft section.
($A_3/A_2$)

As described previously, the microneedle has the base section, the shaft section for supporting most of a drug, which is mounted on the base section, and the top section for puncturing the skin, which is formed on the shaft section, and all of the three sections are unified.

The microneedle preferably satisfies the following expression (6)

$$1.2 \leq A_3/A_2 \leq 10 \tag{6}$$

($A_3$: area of top surface of base section, $A_2$: area of bottom surface of shaft section)

Since the area ($A_3$) of the top surface of the base section is larger than the area ($A_2$) of the bottom surface of the shaft section, when a drug is loaded, it can be closely adhered to the top surface of the base section to be fixed, thereby making it possible to reduce the amount of the drug fixed near the top section. Thereby, the amount of the drug to be loaded can be increased without impairing puncture property. $A_3/A_2$ is more preferably 1.2 to 3. When this value is too small, a sufficient amount of the drug fixed on the base section cannot be ensured and when the value is too large, the amount of the drug loaded on the shaft section is reduced, whereby even when the microneedle is punctured, the amount of the drug able to be directly injected into the body is reduced.

(Supporting Microneedle)

The present invention is a microneedle in which a solid composition comprising a drug is fixed to the side surface of the shaft section. The content of the drug in the solid composition is preferably 5 to 90 parts by weight, more preferably 10 to 80 parts by weight based on 100 parts by weight of the solid composition.

The solid composition preferably comprises a water-soluble polymer as a binder component. Although the water-soluble polymer is not particularly limited, a water-soluble polymer which has little dermal irritancy is preferably used.

Figure 3:
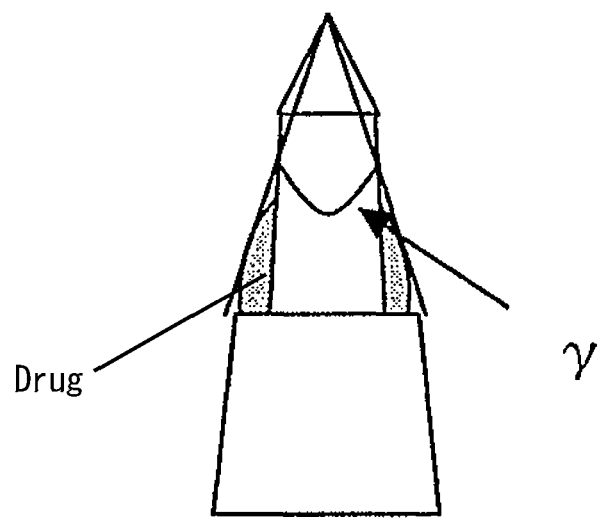
FIG. 3 is a schematic diagram of the microneedle supporting a drug.
Figure 4:
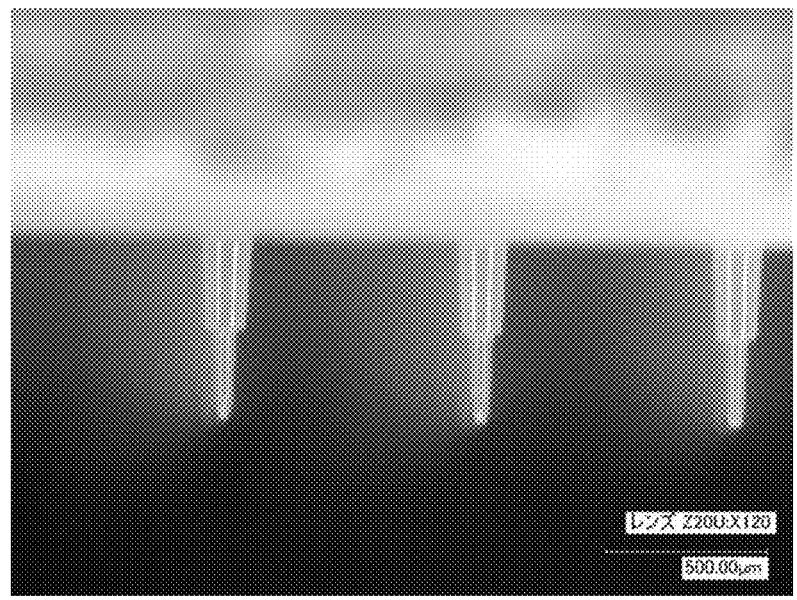
FIG. 4 shows a microneedle before immersion in Example 4.
Figure 5:
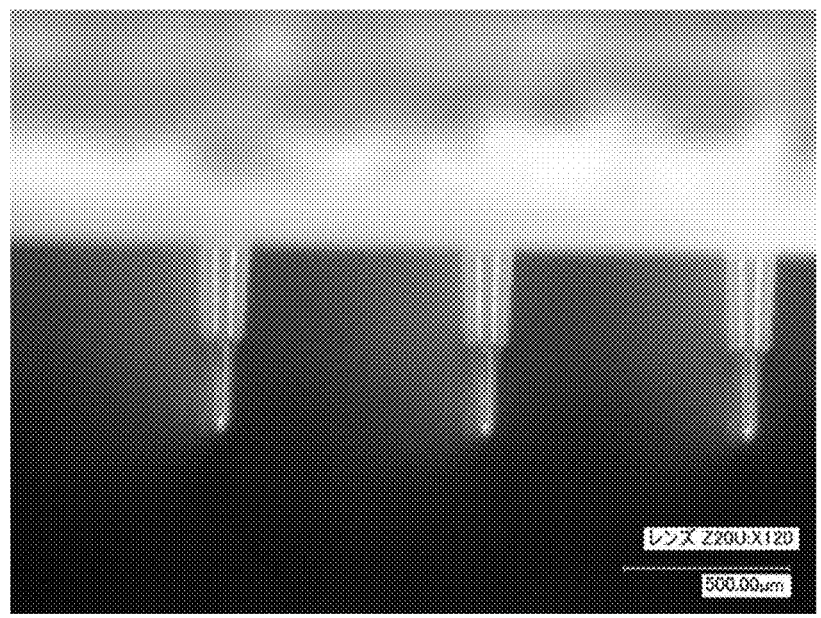
FIG. 5 shows the microneedle after first time of immersion in Example 4.
Figure 6:
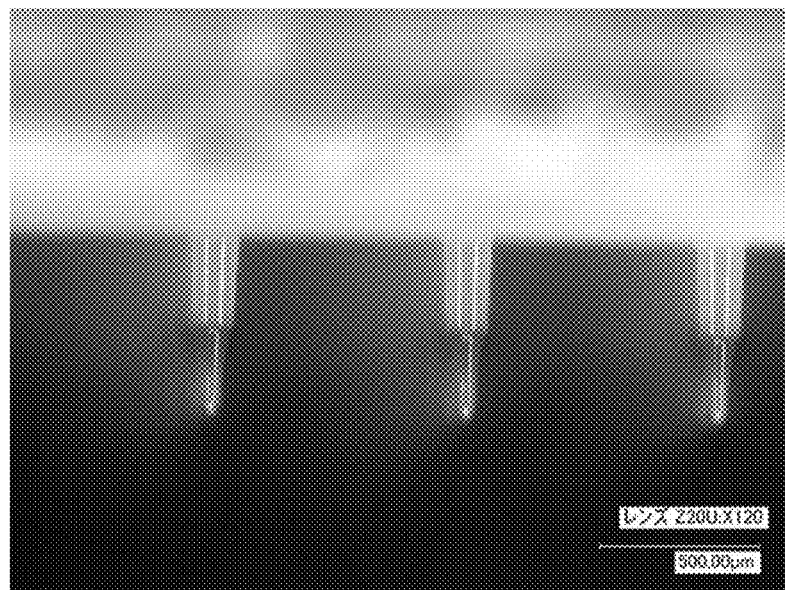
FIG. 6 shows the microneedle after second time of immersion in Example 4.
Figure 7:
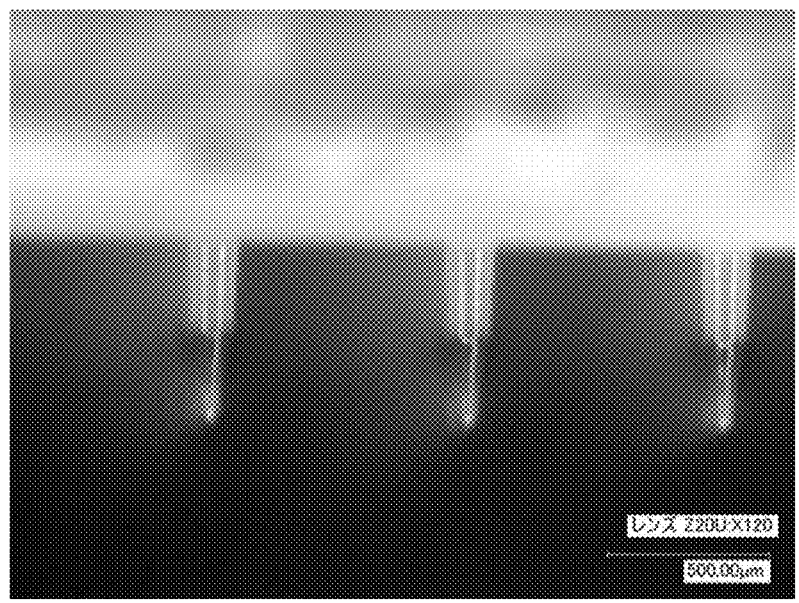
FIG. 7 shows the microneedle after third time of immersion in Example 4.
Figure 8:
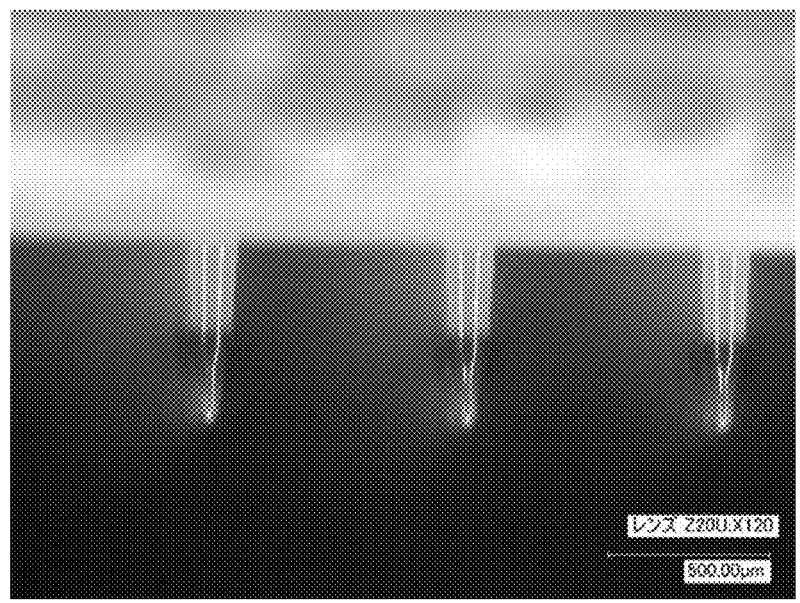
FIG. 8 shows the microneedle after fourth time of immersion in Example 4.
Figure 9:
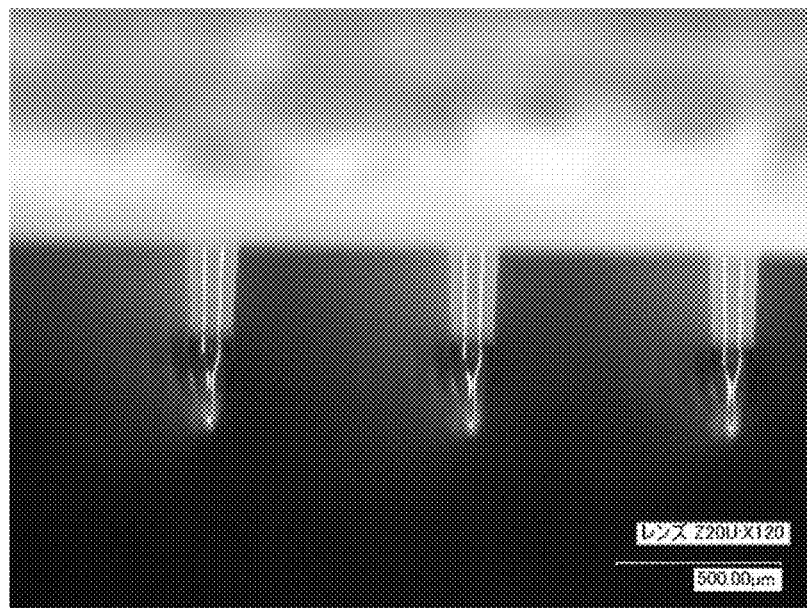
FIG. 9 shows the microneedle after fifth time of immersion in Example 4.
Figure 10:
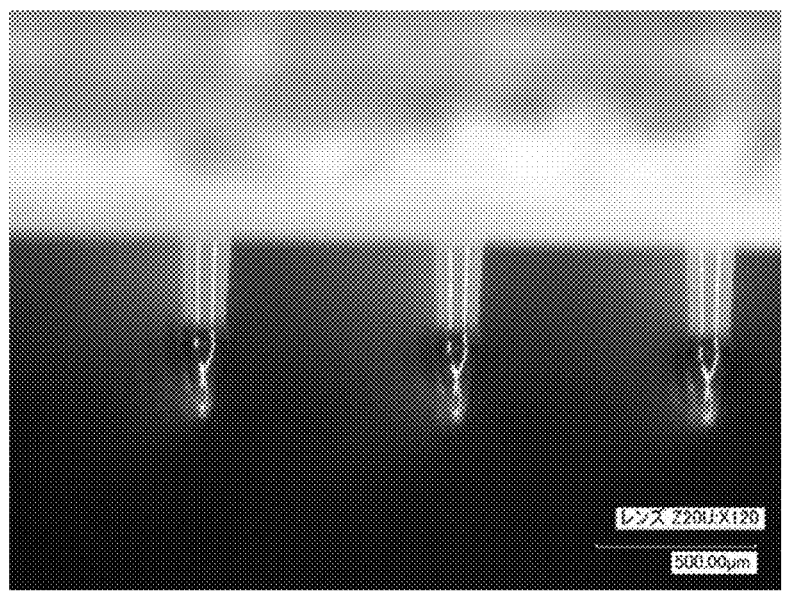
FIG. 10 shows the microneedle after sixth time of immersion in Example 4.
Figure 11:
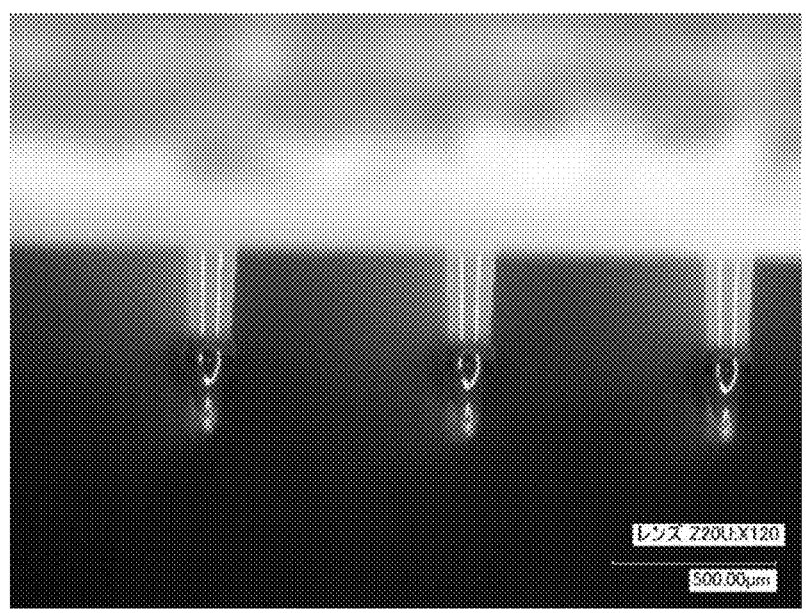
FIG. 11 shows the microneedle after seventh time of immersion in Example 4.

When the drug is fixed to the microneedle, the microneedle has an outer shape in accordance with the fixed state of the drug. The microneedle of the present invention may take a shape shown in FIG. 3. When the drug is fixed to the shaft section and rarely to the top section, the microneedle can ensure almost the same level of horn puncture property as that of a microneedle supported with no drug. After the drug is supported, desirably, the fixed drug does not project from the angle of the top section after coating.

The microneedle supporting a drug of the present invention satisfies the following expression (5), preferably the following expression (5-i), more preferably the following expression (5-ii). When the angle of the microneedle supporting a drug of the present invention falls within the range of the following expression (5), the drug can be loaded without impairing puncture property The microneedle supporting a drug of the present invention preferably satisfies the following expression (6) from the viewpoint of puncture property and the amount of the loaded drug. Further, the microneedle supporting a drug of the present invention preferably satisfies the following expression (7) from the viewpoints of puncture property and the amount of the loaded drug.

$$10° \leq \gamma \leq 60° \tag{5}$$

γ is the angle formed by tangent lines connecting the apex of the top section and the surface of the solid composition fixed to the side surface of the shaft section.

$$10° \leq \gamma \leq 50° \tag{5-i}$$

$$10° \leq \gamma \leq 45° \tag{5-ii}$$

$$\alpha \leq \delta \leq 60° \tag{6}$$

δ is the angle formed by lines connecting the apex of the top section and the surface of the solid composition fixed to the top section.

$$\gamma \geq \delta \tag{7}$$

(Drug)

Biologically active agents such as hormones and vaccines are used as the drug. Specific examples of the drug include growth hormone release hormone (GHRH), growth hormone release factor (GHRF), insulin, insultropin, calcitonin, octreotide, endorphin, TRN, NT-36 (chemical name: N-[[(s)-4-oxo-2-azetidinyl]carbonyl]-L-histidyl-L-prolinamide), liprecin, pituitary hormones (e.g., HGH, HMG, desmopressin acetate, etc), follicle luteoids, aANF, growth factors such as growth factor releasing factor (GFRF), bMSH, GH, somatostatin, bradykinin, somatotropin, platelet-derived growth factor releasing factor, asparaginase, bleomycin sulfate, chymopapain, cholecystokinin, chorionic gonadotropin, erythropoietin, epoprostenol (platelet aggregation inhibitor), glucagon, HCG, hirulog, hyaluronidase, interferon α, interferon β, interferon γ, interleukins, interleukin-10 (IL-10), erythropoietin (EPO), granulocyte macrophage colony stimulating factor (GM-CSF), granulocyte colony stimulating factor (G-CSF), glucagon, leutinizing hormone releasing hormone (LHRH), LHRH analogs (such as goserelin, leuprolide, buserelin, triptorelin, gonadorelin, and napfarelin, menotropins (urofollitropin (FSH) and LH)), oxytocin, streptokinase, tissue plasminogen activator, urokinase, vasopressin, deamino [Val4, D-Arg8] arginine vasopressin, desmopressin, corticotropin (ACTH), ACTH analogs such as ACTH (1-24), ANP, ANP clearance inhibitors, angiotensin II antagonists, antidiuretic hormone agonists, bradykinin antagonists, ceredase, CSI's, calcitonin gene related peptide (CGRP), enkephalins, FAB fragments, IgE peptide suppressors, IGF-1, neurotrophic factors, colony stimulating factors, parathyroid hormone and agonists, parathyroid hormone antagonists, parathyroid hormone (PTH), PTH analogs such as PTH (1-34), prostaglandin antagonists, pentigetide, protein C, protein S, renin inhibitors, thymosin α-1, thrombolytics, TNF, vasopressin antagonists analogs, α-1 antitrypsin (recombinant), and TGF-β.

The drug is also selected from the group consisting of antigens in the form of proteins, polysaccharide conjugates, oligosaccharides and lipoproteins. These subunit vaccines include *Bordetella pertussis* (recombinant PT accince—acellular), *Clostridium tetani* (purified, recombinant), *Corynebacterium diptheriae* (purified, recombinant), *Cytomegalovirus* (glycoprotein subunit), group A *streptococcus* (glycoprotein subunit, glycoconjugate group A polysaccharide with tetanus toxoid, M protein/peptides linked to toxing subunit carriers, M protein, multivalent type-specific epitopes, cysteine protease, C5a peptidase), hepatitis B virus (recombinant Pre S1, Pre-S2, S, recombinant core protein), hepatitis C virus (recombinant—expressed surface proteins and epitopes), human papillomavirus (Capsid protein, TA-GN recombinant protein L2 and E7 [from HPV-6], MEDI-501 recombinant VLP L1 from HPV-11, quadrivalent recombinant BLP L1 [from HPV-6], HPV-11, HPV-16, and HPV-18, LAMP-E7 [from HPV-16]), *Legionellapneumophila* (purified bacterial surface protein), *Neisseria meningitides* (glycoconjugate with tetanus toxoid), *Pseudomonas aeruginosa* (synthetic peptides), *rubella* virus (synthetic peptide), *Streptococcus pneumoniae* (glyconconjugate [1, 4, 5, 6B, 9N, 14, 18C, 19V, 23F] conjugated to meningococcal B OMP, glycoconjugate [4, 6B, 9V, 14, 18C, 19F, 23F] conjugated, to CRM197, glycoconjugate [1, 4, 5, 6B, 9V, 14, 18C, 19F, 23F] conjugated to CRM1970, *Treponema pallidum* (surface lipoproteins), *Varicella zoster* virus (subunit, glycoproteins) and *Vibrio cholerae* (conjugate lipopolysaccharide).

Adrenaline, nicotine, bisphosphonates and fentanyl are also included as the drug.

(Surface Roughness)

The surface roughness of the shaft section of the microneedle satisfies preferably 5 nm≤Rz≤10 μm, more preferably 50 nm≤Rz≤5 μm. When the surface roughness of the shaft section is high at the time of supporting a drug solution, the amount of the drug to be supported increases advantageously. When the surface roughness is high, the shaft section has the effect of preventing spheroidizing by the surface tension of the drug solution at the time of supporting the drug. The limit of surface roughness is a value right before the occurrence of deformation, breakage and the reduction of yield as it becomes release resistance at the time of molding. Unevenness may be made by using machining traces intentionally. Rz is a value measured in accordance with JIS B0601-2001.

(Thermoplastic Resin)

The microneedle and the microneedle array preferably contain a thermoplastic resin as the main component. The content of the thermoplastic resin in the microneedle and the microneedle array is preferably not less than 50 wt %, more preferably not less than 90 wt %, much more preferably 100 wt %.

The thermoplastic resin is preferably at least one selected from the group consisting of polycarbonates, polypropylene, cycloolefin polymers, cycloolefin copolymers, polyethylene terephthalate, acrylic resin, polyphenylene sulfide, polyether ether ketone, polybutylene terephthalate, polybutylene naphthalate and polyethylene naphthalate.

The microneedle and the microneedle array preferably contain a biodegradable resin as the main component.

The biodegradable resin is preferably at least one selected from the group consisting of polyglycolic acid, polylactic acid, stereocomplex polylactic acid, plant-derived polycarbonate resin and polybutylene succinate.

The plant-derived polycarbonate resin is a resin comprising a plant-derived raw material as the main component, preferably a polycarbonate resin containing a carbonate constituent unit represented by the following formula (a).

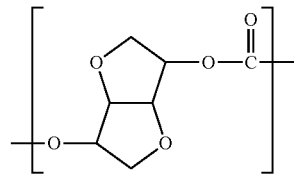

The polyglycolic acid resin used in the present invention is preferably a homopolymer of glycolic acid consisting of a glycolic acid recurring unit, that is, glycolic acid homopolymer (PGA, including a ring-opening polymer of glycolide (GL) which is a bimolecular cyclic ester of glycolic acid). More specifically, it may be a copolymer of another comonomer, that is, a glycolic acid copolymer as long as it contains not less than 90 wt % of the above recurring unit. The polyglycolic acid has a molecular weight (Mw (weight average molecular weight) in terms of polymethyl methacrylate) measured by GPC using a hexafluoroisopropanol solvent of preferably 100,000 to 800,000, particularly preferably 130,000 to 750,000. When the molecular weight is too low, the obtained molded product tends to become unsatisfactory in terms of strength. When the molecular weight is too high, melt extrusion or molding may become difficult.

The thermoplastic resin used in the present invention may contain additives such as a stabilizer, reinforcing agent and plasticizer. Examples of the stabilizer include an antioxidant, heat stabilizer, hydrolysis resisting agent, electron beam stabilizer and ultraviolet stabilizer. Examples of the reinforcing agent include inorganic fillers and organic fillers. Additives which do no harm to a living body are preferably used.

<Production Process of Microneedle>

The microneedle and the microneedle array can be manufactured by the following steps. An apparatus described in JP-A 2008-49646 may be used as the molding machine.

(Melting Step)

This is the step of heating the resin at a temperature of 200 to 300° C. to melt it (Coating Step)

This is the step of applying the molten resin to a mold kept at 100 to 250° C.

The temperature of the mold is preferably raised at a rate of 5° C./sec to 10° C./sec. In the process of the present invention, after the resin is applied to the mold kept at 100 to 250° C. and molded, the temperature of the mold is reduced to demold a molded product. That is, when molding is carried out continuously, the temperature of the mold is increased and decreased repeatedly. Therefore, as the temperature elevation rate and the temperature reduction rate are high, the cycle time is shortened advantageously. To achieve the above temperature elevation time, electromagnetic induction heating is preferably employed. Since the electromagnetic induction heating does not increase the temperature of the entire mold but allows for local temperature elevation, energy required for molding can be reduced.

(Molding Step)

This is the step of molding by applying a pressure of 0.1 to 30 MPa for 5 to 200 seconds.

(Demolding Step)

The molded product is taken out from the mold by reducing the temperature to 50 to 100° C. at a rate of 5° C./sec to 10° C./sec.

In the above process, the resin temperature elevation time is shortened and the molding time is short by using the molten resin as compared with a process in which a film is imprinted. The inside temperature of the resin is uniform and predetermined, thereby making high-accuracy transfer possible. For example, as for the production of a mold for molding, a method of manufacturing a mold by cutting a metal to produce a master and inverting it by electrocasting is employed. The method of manufacturing a mold is not limited to this (Step of Supporting a Drug)

The solid composition containing a drug can be fixed to the side surface of the shaft section by immersing the microneedle or the microneedle array in a solution containing the drug, pulling it up and drying it. Therefore, immersion and drying are preferably repeated to achieve a desired amount of the supported drug.

<Microneedle Array>

In the present invention, a microneedle array including a plurality of the above microneedles may be used The microneedle array has both safety and simplicity and a microneedle density of preferably 1 to 1,000 needles/cm$^2$, more preferably 100 to 1,000 needles/cm$^2$ because it can administer a predetermined drug without pain. Although the amount of the drug to be supported can be increased as the density becomes higher, larger force is required to push the microneedle and the microneedle array as the density becomes higher. The density is preferably a value at which painless pressing force is obtained.

Pressing force is force required to puncture the skin with the microneedle and the microneedle array. If it is too large, a patient feels pain at the time of pushing. Therefore, pressing force is preferably 1 to 10 N, more preferably 1 to 5 N. Since pressing force is limited, a microneedle which is punctured smoothly with a small load is required.

The microneedle array preferably has a puncture ratio of not less than 80% when it is pushed into a depth of 10 mm from the surface of the skin. When the microneedle array is pressed against the skin with 5 newton (N) force applied to a substrate having a diameter of 10 mm, it preferably has a puncture ratio of not less than 80%.

<Microneedle Device>

The present invention includes a microneedle device containing a microneedle or microneedle array supporting a drug and an applicator for administering the drug to a living body. As the applicator, a known applicator which pushes the microneedle array manually or mechanically may be used <Method of Administering a Drug>

According to the present invention, there is provided a method of administering a drug by puncturing the surface of the skin with the microneedle or the microneedle array supporting the drug. The drug is selected from biologically active agents, vaccines and the like as described above. The administration method of the present invention can be applied to living bodies such as mammals including cows, pigs and humans. According to the administration method of the present invention, the microneedle or the microneedle array can be thrust into a living body without pain with small force.

EXAMPLES

Examples of the present invention will be given below.

Example 1 (Two-stage Needle: PGA, Normal Fixation)

The microneedle was manufactured as follows. A mold was manufactured by cutting a metal to produce a master which is the basis of the mold and inverting the master by nickel electrocasting. As for the shape of the microneedle, the tip diameter ($D_0$) was 7 μm, the diameter ($D_1$) of the bottom surface of the top section was 60 μm, the diameter ($D_2$) of the bottom surface of the shaft section was 100 μm, the diameter ($D_4$) of the bottom surface of the base section was 150 μm, the overall height (H) was 600 μm, the height ($H_1$) of the top section was 65 μm, the height ($H_2$) of the shaft section was 240 μm, the tip apex angle (α) was 45°, and 120 needles were used.

For the molding of the microneedle, Micro-Nano Melt Transcription Molding Machine (registered trademark) of The Japan Steel Works, Ltd. was used. Polyglycolic acid (PGA) was used as the resin, molten at 260° C. and applied to a 200° C. mold. Then, the resin was pressed at a pressure of 20 MPa for about 30 seconds, the obtained mold was cooled to 80° C., and a microneedle array was taken out from the mold. The obtained microneedle array was observed through a laser microscope to confirm that the shape of the mold was accurately transferred without the breakage and deformation of the microneedle array.

(Support of Drug) 1.5 g of polyvinyl pyrrolidone (K20) and 0.1 g of Blue No. 1 as a drug were dissolved in 8.4 g of water. The resulting solution was applied to a metal plate to form a liquid film. The molded microneedle was fixed to an XYZ stage, the top section of the microneedle was immersed in the above liquid film to a height of the base section or to a depth of about 0.3 mm while it was observed through a microscope, and the microneedle was pulled up immediately and dried for 1 minute. This operation was repeated 5 times to fix the drug.

(Evaluation)

As for the obtained microneedle array, (1) the amount of the fixed drug, (2) the angle (γ) between the fixed material and the tip, (3) surface roughness and (4) puncture property were evaluated. As for the measurement of γ, when the adhered drug projected above from the inclined extension line of the top section of the microneedle, the angle formed by tangent lines connecting the apex of the top section and the fixed material was measured. When the amount of the adhered drug was small and the fixed material of the drug was existent below the inclined extension line of the top section of the microneedle, the angle formed by lines connecting the top section and the most projecting part of the fixed material was measured.

The evaluation of the angle (γ) between the fixed material and the tip is 45° or less as shown in Table 1 and does not differ from the value (45°) of the tip apex angle (α) before coating. This makes it clear that a part except for the top section of the microneedle can bring in the drug adhered to the top section based on the shape of each of the two-stage needles of the microneedle array of the present invention when the microneedle is immersed in the drug solution and pulled up, whereby the drug is hardly fixed to the top section with the result that the tip of the microneedle is exposed and the sharp top section can be maintained even after the application of the drug solution.

After the microneedle was pressed against the abdomen of a rat whose hair has been shaved for 10 seconds, the needle was observed to check whether a pigment peeled off or not so to evaluate puncture property based on the following criteria.

◯: peeling of pigment is observed in 70% or more of needles
Δ: peeling of pigment is observed in 20% or more of needles
×: peeling of pigment is observed in less than 20% of needles

Example 2 (Two-stage Needle: SUS, Normal Fixation)

A microneedle having the same shape as that of Example 1 was manufactured by cutting stainless steel, and a drug was fixed to the microneedle by the same method as in Example 1 to make the above evaluations in the same manner as in Example 1.

Example 3 (Two-stage Needle: PGA, Fixation of a Small Amount)

The microneedle manufactured in Example 1 was used to fix a drug by the same method as in Example 1 but the number of times of immersion was 3. The above evaluations were made The results are shown in Table 1. In Table 1, a describing method for specifying the shape of the two-stage needle of the present invention is employed and does not match a method for a one-stage needle. For example, when the one-stage needle is described by the method for the two-stage needle, $D_2=D_3$. In the case of the two-stage needle, $D_2<D_3$.

Example 4

The microneedle was manufactured as follows.

A mold was manufactured by cutting a metal to produce a master which is the basis of the mold and inverting the master by nickel electrocasting. As for the shape of the microneedle, the tip diameter ($D_0$) was 7 μm, the diameter ($D_1$) of the bottom surface of the top section was 60 μm, the diameter ($D_2$) of the bottom surface of the shaft section was the diameter ($D_4$) of the bottom surface of the base section was 150 μm, the overall height (H) was 600 μm, the height ($H_1$) of the top section was 65 μm, the height ($H_2$) of the shaft section was 235 μm the tip apex angle (α) was 45°, and 120 needles were For the molding of the microneedle, Micro-Nano Melt Transcription Molding Machine (registered trademark) of The Japan Steel Works, Ltd. was used Polyglycolic acid (PGA) was used as the resin, molten at 260° C. and applied to a 200° C. mold. Then, the resin was pressed at a pressure of 20 MPa for about 30 seconds, the mold was cooled to 80° C., and a microneedle array was taken out from the mold. The obtained microneedle array was observed through a laser microscope to confirm that the shape of the mold was accurately transferred without the breakage and deformation of the microneedle array.

15 g of polyvinyl pyrrolidone (K90), 1 g of Blue No 1 and 10 g of lidocaine hydrochloride were dissolved in 74 g of purified water to prepare a sample solution.

The prepared sample solution was filled into a groove having a depth of 400 μm and a width of 400 μm, and the microneedle manufactured as described above was immersed in the sample solution until the drug solution was fixed to the base section and dried for 1 minute. Immersion and drying were repeated 7 times to observe the microneedle after the fixation of the drug through a microscope (FIGS. 4 to 11). The angle (γ(°)) between the fixed material and the tip was evaluated in the same manner as in Example 1.

The amount of lidocaine hydrochloride was determined from the microneedle after 7 times of immersion.

It was confirmed from the shape of the microneedle after the fixation of the drug that most of the drug was first supported by the base section and then by the shaft section as immersion was repeated multiple times.

Since the drug tends to be supported by a stepped part and rarely supported by the top section of the needle, it is understood that the stepped part can be used as a site for the storage of the drug and this design hardly impairs the shape of the tip of the needle.

TABLE 1

|  | unit | Example 1 | Example 2 | Example 3 | Example 4 |
| --- | --- | --- | --- | --- | --- |
| Determination of amount of fixed drug | μg/needle | 1.14 | 1.14 | 0.56 | 118 |
| Tip apex angle: α | ° | 45 | 45 | 45 | 45 |
| angle between side surface of shaft section and top surface of base section: β | ° | 85 | 85 | 85 | 88 |
| angle between fixed material and tip: γ | ° | 45 | 45 | 30 | 26-44 |
| overall height: H | μm | 600 | 600 | 600 | 600 |
| height of top section: $H_1$ | μm | 65 | 65 | 65 | 65 |
| height of shaft section: $H_2$ | μm | 240 | 240 | 240 | 235 |
| tip diameter: $D_0$ | μm | 7 | 7 | 7 | 7 |
| diameter of bottom surface of top section: $D_1$ | μm | 60 | 60 | 60 | 60 |
| diameter of bottom surface of shaft section: $D_2$ | μm | 100 | 100 | 100 | 75 |
| diameter of top surface of base section: $D_3$ | μm | 125 | 125 | 125 | 125 |
| diameter of bottom surface of base section: $D_4$ | μm | 150 | 150 | 150 | 150 |
| $H/D_4$ | — | 4 | 4 | 4 | 4 |
| $A_3/A_2$ | — | 1.6 | 1.6 | 1.6 | 2.8 |
| surface roughness (nm) | nm | 300 | 300 | 300 | — |
| puncture property | — | ⊙ | ◯ | ◯ | — |
| raw material | — | PGA | SUS | PGA | PGA |

TABLE 2

| | Number of times of immersion | | | | | | |
|---|---|---|---|---|---|---|---|
| | 1 | 2 | 3 | 4 | 5 | 6 | 7 |
| Angle between fixed material and tip: γ (°) | 26 | 28 | 33 | 34 | 38 | 41 | 44 |
| Amount of lidocaine hydrochloride (μg) | — | — | — | — | — | — | 118 |

Examples 5 to 7 Comparative Examples 1 to 3

20 g of polyvinyl pyrrolidone (K90), 1 g of Blue No. 1 and 10 g of lidocaine hydrochloride were dissolved in 69 g of purified water to prepare a sample solution.

The prepared sample solution was filled into a groove having a depth of 500 μm and a width of 400 μm, and a stainless steel microneedle shown in Table 3 was immersed in the sample solution in the groove up to its base section or to a depth of about 0.3 mm and dried for 2 minutes. Immersion and drying were repeated several times (4 times in Example 5, 4 times in Example 6, 4 times in Example 7, 10 times in Comparative Example 1 and 5 times in Comparative Examples 2 and 3). In Comparative Example 3, a groove having a depth of 500 μm and a width of 700 μm was used to apply the drug.

TABLE 3

| | unit | C. Ex. 1 | Ex. 5 | Ex. 6 | Ex. 7 | C. Ex. 2 | C. Ex. 3 |
|---|---|---|---|---|---|---|---|
| Tip apex angle: α | ° | 45 | 45 | 45 | 45 | 45 | 45 |
| angle between side surface of shaft section and top surface of base section: β | ° | | 88 | 88 | 88 | 88 | 88 |
| overall height: H | μm | 600 | 600 | 600 | 600 | 600 | 600 |
| height of top section: $H_1$ | μm | 65 | 65 | 65 | 25 | 65 | 65 |
| height of shaft section: $H_2$ | μm | 535 | 235 | 235 | 275 | 235 | 235 |
| tip diameter: $D_0$ | μm | 7 | 7 | 7 | 7 | 7 | 7 |
| diameter of bottom surface of top section: $D_1$ | μm | 60 | 60 | 60 | 25 | 60 | 60 |
| diameter of bottom surface of shaft section: $D_2$ | μm | — | 75 | 75 | 50 | 75 | 75 |
| diameter of top surface of base section: $D_3$ | μm | — | 125 | 100 | 55 | 235 | 410 |
| diameter of bottom surface of base section: $D_4$ | μm | — | 150 | 120 | 80 | 260 | 435 |
| $H/D_4$ | — | — | 4 | 5 | 7.5 | 2.3 | 1.4 |
| $A_3/A_2$ | — | 1 | 2.8 | 1.8 | 1.2 | 9.8 | 29.9 |

Ex.: Example
C. Ex.: Comparative Example

The microneedle after the fixation of the drug was observed through a microscope to evaluate the angle (γ(°)) between the fixed material and the tip in the same manner as in Example 1. The amount of the supported drug was measured from the microneedle.

Further, the puncture performance of the microneedle was evaluated by the following method (see FIG. 12).
1. The abdominal skin of Wistar 5w ♂ was placed and fixed on a silicone sheet (thickness of 5 mm, hardness of 50°).
2. The microneedle was inserted into the skin at a rate of 1-mm/min and stopped when stress became 0.05N.
3. The microneedle was removed, and 2% gentian violet was dropped on the punctured site
4. The drug was allowed to stand for a few minutes.
5. The punctured site was cleaned with ethanol.
6. The existence or absence of a puncture mark was checked by a stereoscopic microscope. ○ indicates that the punctured site was stained and x indicates that the punctured site was not stained.

Figures 12, 13:
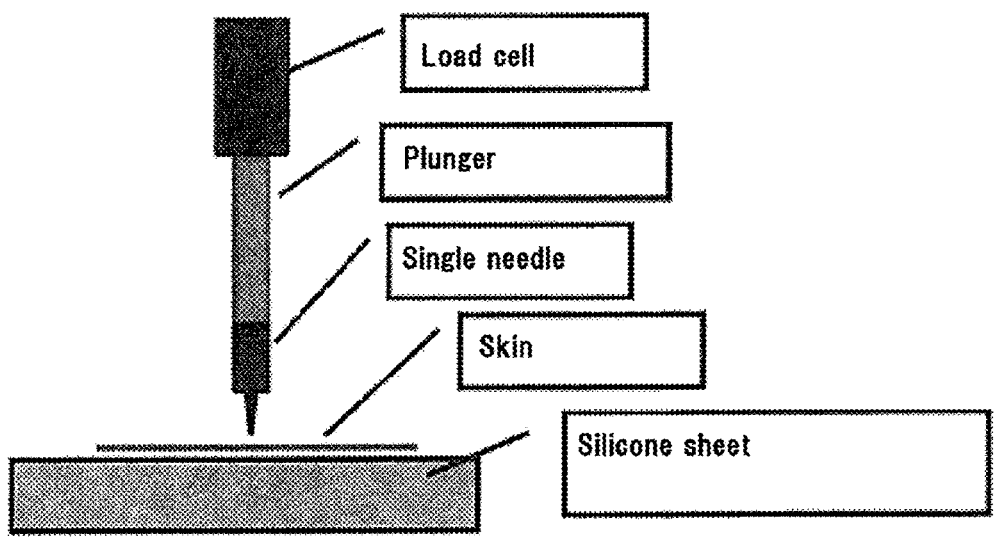
FIG. 12 is a schematic diagram showing a method of evaluating puncture performance in Examples 5 to 7 and Comparative Examples 1 to 3.
FIG. 13 shows the evaluation results of Examples 5 to and Comparative Examples 1 to 3.

The above evaluation results are shown in FIG. 13. That is, as shown in FIG. 13, puncture property is satisfactory until the value of γ is up to 60°. It was found that the amount of the drug able to be supported differs by the shape of the microneedle even when the number of times of application is the same. That is, when $H/D_4$ is 3 to 5, about 1 μg of the drug can be supported whereas when $H/D_4$ is 7.5, the amount of the drug is greatly reduced to about 0.1 μg.

Examples 8 and 9 (Two-stage Needle)

A microneedle array molded by the same molding method as in Example 1 was used except that the tip diameter ($D_0$) was 7 μm, the diameter ($D_1$) of the bottom surface of the top section was 60 μm, the diameter ($D_2$) of the bottom surface of the shaft section was 75 μm, the diameter ($D_4$) of the bottom surface of the base section was 150 μm, the overall height (H) was 600 μm, the height ($H_1$) of the top section was 65 μm, the height ($H_2$) of the shaft section was 235 μm, the tip apex angle (α) was 45°, and 120 microneedles were arranged in a matrix of 12×10 at intervals of 800 μm as for the shape of the microneedle array. The shape of the microneedle is shown in Table 4.

Coating was carried out by the following method.
1.0 g of polyvinyl pyrrolidone (K90), 1.0 g of OVA and 0.1 g of Blue No 1 were dissolved in 7.9 g of purified water to prepare a sample solution. The prepared sample solution was filled into a groove having a depth of 400 μm and a width of 400 μm, and the microneedle was immersed in the sample solution in the groove up to its base section or to a depth of about 0.3 mm and dried for 1 minute. Immersion and drying were repeated a number of times shown in Table 4 to manufacture microneedles which differed in the amount of the supported drug.

Figure 14:
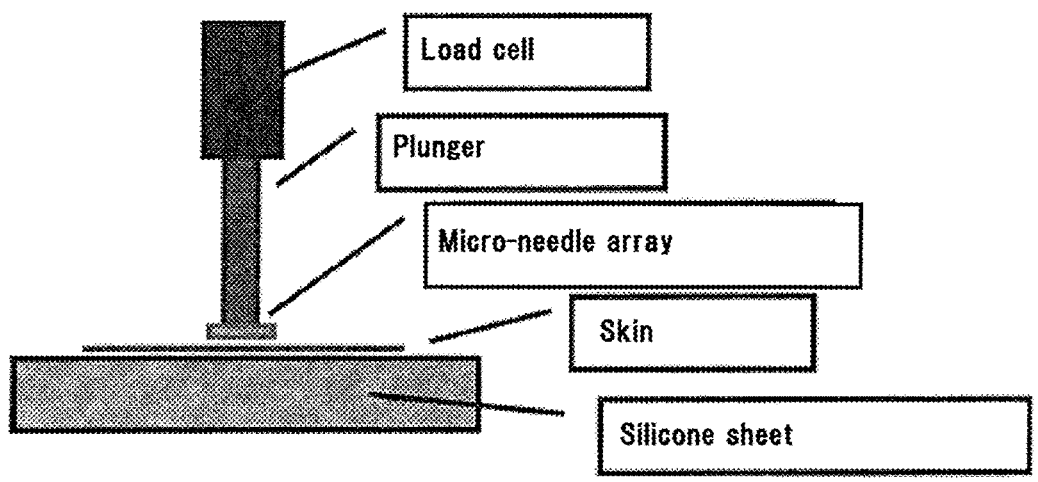
FIG. 14 is a schematic diagram showing a method of evaluating puncture performance in Examples 8 and 9 and Comparative Examples 4 to 6.

Further, the puncture performance was evaluated by the following method (FIG. 14).
1. The abdominal skin of Wistar 5w ♂ was placed and fixed on a silicone sheet (thickness of 5 mm, hardness of 50°).
2. The microneedle was inserted into the skin at a rate of 1 mm/min and stopped when stress became 0.03N/needle.
3. The microneedle was removed, and 2% gentian violet was dropped on the punctured
4. The drug was allowed to stand for a few minutes.
5. The punctured site was cleaned with ethanol.
6. The existence or absence of a puncture mark was checked by a stereoscopic microscope. ○ indicates that the punctured site was stained and x indicates that the punctured site was not stained.

Comparative Examples 4, 5 and 6 (One-stage Needle)

Microneedles were manufactured in the same manner as in Example 1. As for the shape of each of the microneedles, the tip diameter ($D_0$) was 7 µm, the diameter ($D_4$) of the bottom surface of the base section was 150 µm, the overall height (H) was 600 µm, the height ($H_1$) of the top section was 65 µm, the tip apex angle (α) was 45°, and 97 needles were used. The shape of the microneedle is shown in Table 4.

The drug was fixed by the same method as in Example 1 and evaluated in the same manner as in Example 1. The evaluation of application and puncture property was carried out in the same manner as in Examples 8 and 9.

Figure 15:
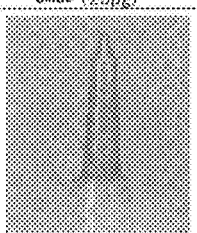
FIG. 15 shows the evaluation results of Examples 8 and Comparative Examples 4 to 6.

The above evaluation results are shown in Table 5 and FIG. 15. As shown by these results, even when 230 µg of the drug is supported by the microneedle array, as shown in FIG. 13 and FIG. 15, γ tends to become large with a one-stage needle and hardly becomes large with a two-stage needle. δ (angle formed by lines connecting the apex of the top section and the surface of a solid composition fixed to the top section) tends to become large with a one-stage needle and hardly becomes large with a two-stage needle likewise. When γ is 60° or more, it is difficult to stab the microneedle and when γ is 70°, puncture property degrades. When δ is 60°, puncture property is satisfactory whereas when δ is 70°, puncture property degrades. That is, when the drug is supported by the microneedle, both γ and δ tend to become large with a single-stage needle whereas the sharpness of the top section of a microneedle tends to be kept and puncture property is satisfactory with a two-stage needle even when the amount of the supported drug is the same.

Thus, it was found that even when the amount of the applied drug is large, the tip angle is easily kept in the two-stage needle. As a result, it was demonstrated that, when the tip angle falls within a predetermined range, if a sufficient amount of a drug is loaded, puncture property is not impaired.

TABLE 4

| | unit | Examples 8 and 9 | Comparative Examples 4, 5 and 6 |
|---|---|---|---|
| Tip apex angle: α | ° | 45 | 45 |
| angle between side surface of shaft section and top surface of base section: β | ° | 87.5 | — |
| overall height: H | µm | 600 | 600 |
| height of top section: $H_1$ | µm | 65 | 65 |
| height of shaft section: $H_2$ | µm | 235 | — |
| tip diameter: $D_0$ | µm | 7 | 7 |
| diameter of bottom surface of top section: $D_1$ | µm | 60 | — |
| diameter of bottom surface of shaft section: $D_2$ | µm | 75 | — |
| diameter of top-surface of base section: $D_3$ | µm | 125 | — |
| diameter of bottom surface of base section: $D_4$ | µm | 150 | 150 |
| $H/D_4$ | — | 4 | 4 |
| $A_3/A_2$ | — | 2.8 | 1 |

TABLE 5

| | Type of needle | number of times of immersion | amount of coating | puncture ratio |
|---|---|---|---|---|
| Ex. 8 | two-stage | 1 | Small (20 µg) | >90% |
| Ex. 9 | two-stage | 7 | Medium (230 µg) | >90% |
| C. Ex. 4 | one-stage | 2 | Small (20 µg) | >90% |
| C. Ex. 5 | one-stage | 10 | Medium (220 µg) | 30% |
| C. Ex. 6 | one-stage | 20 | Large (1200 µg) | 0% |

Effect of the Invention

Since the microneedle and the microneedle array constituting the present invention have a two-stage needle shape, when the microneedle is immersed in a drug solution and pulled up, a stepped part can bring in the drug solution adhered to the top section. As a result, the stepped part can be used as a site for the storage of the drug and even when a large amount of the drug is supported, the tip of the microneedle can be exposed and a sharp top section can be kept after the application of the drug solution.

The two-stage shape of the microneedle shown in FIG. 1 is a needle shape that makes it difficult to fix the drug to the top section of the microneedle. As a result, the microneedle and the microneedle array of the present invention can be inserted into the epidermal layer of a Patient smoothly as a sharp top section is kept, has both safety and simplicity and can administer a predetermined drug without pain. Since the microneedle and the microneedle array constituting the present invention are excellent in the support capacity of a drug, it can administer the drug efficiently.

Industrial Feasibility

The microneedle and the microneedle array of the present invention can be used not only for medical purpose but also in MEMS devices which require a fine needle structure, drug discovery and cosmetics.

The invention claimed is:

1. A microneedle for administering a drug transdermally, which comprises a top section, a shaft section and a base section, wherein
    (i) the tip apex angle (α) is 15 to 60°;
    (ii) the tip diameter ($D_0$) is 1 to 20 µm;
    (iii) the area ($A_3$) of the top surface of the base section is larger than the area ($A_2$) of the bottom surface of the shaft section;
    (iv) the following expressions (1) and (2) are satisfied:

$$H/D_4 \geq 3 \quad (1)$$

(H is the overall height, and $D_4$ is the diameter of the bottom surface of the base section);

$$\beta \geq 90 - 0.5\alpha \quad (2)$$

(β is the angle between the side surface of the shaft section and the top surface of the base section, and α is the tip apex angle); and
    (v) a solid composition containing the drug is fixed to the side surface of the shaft section and the following expression (5) is satisfied:

$$10° \leq \gamma \leq 60° \quad (5)$$

(γ is the angle formed by tangent lines connecting the apex of the top section and the surface of the solid composition fixed to the side surface of the shaft section).

2. The microneedle according to claim 1, wherein the solid composition contains a water-soluble polymer as a binder component.

3. The microneedle according to claim 1 which has an overall height (H) of 120 to 800 µm.

4. The microneedle according to claim 1 which satisfies the following expression (6):

$$1.2 \leq A_3/A_2 \leq 10 \quad (6)$$

($A_3$ is the area of the top surface of the base section, and $A_2$ is the area of the bottom surface of the shaft section).

5. The microneedle according to claim 1, wherein the height ($H_3$) of the base section is 100 to 500 μm.

6. The microneedle according to claim 1 which contains a thermoplastic resin as the main component.

7. The microneedle according to claim 6, wherein the thermoplastic resin is at least one selected from the group consisting of polycarbonates, polypropylene, cycloolefin polymers, cycloolefin copolymers, polyethylene terephthalate, acrylic resin, polyphenylene sulfide, polyether ether ketone, polybutylene terephthalate, polybutylene naphthalate and polyethylene naphthalate.

8. The microneedle according to claim 1 which contains a biodegradable resin as the main component.

9. The microneedle according to claim 8, wherein the biodegradable resin is at least one selected from the group consisting of polyglycolic acid, polylactic acid, stereocomplex polylactic acid, plant-derived polycarbonate resin and polybutylene succinate.

10. A microneedle array including the microneedles of claim 1 at a density of 100 to 1,000 needles/cm$^2$.

11. A microneedle device including the microneedle array of claim 10 and an applicator for administering to a living body.

12. A method of administering a drug, comprising the step of puncturing the surface of the skin with the microneedle array of claim 10.

* * * * *